United States Patent [19]

Ushio et al.

[11] Patent Number: 5,518,990
[45] Date of Patent: May 21, 1996

[54] METHOD FOR PREVENTING EMERGENCE OF ALGAE AND ANTIALGAL COMPOSITION

[75] Inventors: Kazumichi Ushio, Nishinomiya; Yoshiki Makimoto, Toyonaka, both of Japan

[73] Assignee: Senju Pharmaceutical Co., Ltd., Osaka, Japan

[21] Appl. No.: 406,810

[22] Filed: Mar. 20, 1995

Related U.S. Application Data

[63] Continuation of Ser. No. 128,727, Sep. 30, 1993, abandoned.

[30] Foreign Application Priority Data

Jul. 15, 1993 [JP] Japan .................... 5-175428

[51] Int. Cl.$^6$ .................... A01N 59/16
[52] U.S. Cl. .................... 504/121; 504/151; 504/159
[58] Field of Search .................... 504/121, 151, 504/159

[56] References Cited

U.S. PATENT DOCUMENTS

| | | | |
|---|---|---|---|
| 2,768,971 | 10/1956 | Jones | 260/553 |
| 3,585,967 | 6/1971 | Kelley et al. | 119/3 |
| 3,623,455 | 11/1971 | Kelley et al. | 119/3 |
| 3,886,904 | 6/1975 | King | 119/3 |
| 3,909,230 | 9/1975 | Krenzer | 71/66 |
| 4,622,060 | 11/1986 | Takematsu et al. | 71/86 |
| 4,840,658 | 6/1989 | Kakisawa et al. | 71/67 |
| 4,849,236 | 7/1989 | Kakimoto et al. | 426/322 |
| 4,976,769 | 12/1990 | Iwasaki | 71/86 |
| 5,158,596 | 10/1992 | Sherba et al. | 71/67 |
| 5,219,825 | 6/1993 | Gressel et al. | 504/117 |
| 5,266,105 | 11/1993 | Tsuneta et al. | 106/16 |

FOREIGN PATENT DOCUMENTS 60-255706  12/1985  Japan .

OTHER PUBLICATIONS

Central Patents Index, Basic Abstracts Journal, Derwent Publications Ltd., London, GB; Class C, AN 21030 K & JP-A-58 010 509 (Dai-Ichi Seimo KK) (1983).

Chemical Patents Index, Documentation Abstracts Journal, Derwent Publications Ltd., London, GB; Class C, AN 248665 & JP-A-3 161 408 (Lion Corp) (1991).

Phycologia (1982), 21(2), 125-30 Coden, Markham et al, "Observations on the effects of germanium dioxide . . . ".

Phycologia (1966), 6(1), 1-12 Coden, Lewin, "Silicon Metabolism in Diatoms. V. Germanium Dioxide . . . ".

Letters in Applied Microbiology, vol. 7, 1988, pp. 87-90, Paterson et al, "Diffusion Gradient plates for herbicide toxicity . . . ".

Wright et al., CA88:184213t, "Interactions of herbicide propanil . . . ". Acta. Phytopathol. Acad. Sci. Hung., 12(1-2), pp. 51-60 (1977).

Maule et al., CA101:224727;, "Herbicidal effects on the population growth . . . ", J. App. Bacteriol. 57(2), 369-79 (1984).

Tanaka et al., CA 84:1245e, "Red Tide Flagellate control . . . ", JP75-107135, Aug. 23, 1975 pp. 1-3.

*Primary Examiner*—Richard L. Raymond
*Assistant Examiner*—Brian G. Bembenick
*Attorney, Agent, or Firm*—Wenderoth, Lind & Ponack

[57] ABSTRACT

A method for inhibiting or preventing emergence and growth of algae, comprising use of a germanium compound and a herbicide, and an antialgal composition comprising a germanium compound and a herbicide. The method of the present invention inhibits and prevents emergence and growth of algae, and can be used safely with little influence on aquatic animals. The method is advantageously used for a fish tank in which fish for appreciation is kept, so as to keep good appearance of the tank and to reduce burden of cleaning the tank by preventing emergence and growth of attached algae. Particularly, the composition for artificial seawater of the present invention shows no toxicity to marine animals to be raised in the artificial seawater prepared using the composition of the invention, and can inhibit and prevent emergence of algae. Therefore, the composition of the invention can be beneficially used for raising, culture, study, and the like of marine animals. Moreover, the composition of the present invention which is coated on a fish net, a hull, or the like can result in inhibition and prevention of emergence and growth of algae in the environment where influence on fish, etc. is very little.

7 Claims, No Drawings

METHOD FOR PREVENTING EMERGENCE OF ALGAE AND ANTIALGAL COMPOSITION

This application is a continuation of now abandoned application Ser. No. 08/128,727, filed Sep. 30, 1993.

FIELD OF THE INVENTION

The present invention relates to a method for inhibiting or preventing emergence anti growth of algae. The present invention also relates to an antialgal composition capable of inhibiting or preventing emergence and growth of algae.

BACKGROUND OF THE INVENTION

Alga is a flora mainly composed of photosynthetic plants which grow in waters such as lake water, swamp water, river water, and ocean water. It also lives in soil or attaches to live on rocks, tree surfaces, body surfaces of animals, and the like besides living under water. Algae are generally classified by color into green algae, brown algae, and red algae, or by characteristics. They may be classified into macroalgae and microalgae as well. Algae have been deeply concerned with mankind from ancient times, and used as beneficial living aquatic resources. However, they also behave unbeneficially when culturing fish or the like in a fishing net or a net-cage by adhering to and growing on a fish net with the result that streams are prevented and fish suffers from oxygen shortage, and when raising aquatic animals under closed environments such as in a fish tank or a culture pond, proliferous microalgae grow to cause pollution of water for raising aquatic animals or diseases of them. In addition, the algae which emerge and grow on the draft of seacrafts can prevent smooth ship navigation.

When raising fish for appreciation in an aquarium or at home, the effect of algae is not only pollution of water for raising aquatic animals as described but also difficulty in removing algae attached and grown on the glass of a fish tank and spoiled appearance of the tank.

When culturing aquatic animals for studying purposes, the growth of microalgae prevents normal growth of aquatic animals being cultured, which in turn markedly affects the results of the study.

Therefore, various algaecides have been studied for inhibiting or preventing emergence and growth of algae, and quaternary ammonium salts such as benzalkonium chloride and chlorine compounds such as sodium hypochlorite have been mainly used. Yet, they are not desirable since they are highly toxic and harmfully affect aquatic animals.

Incidentally, germanium which interrupts intake of silicon into cell membranes of diatom to inhibit growth shows a preventive effect on the growth of some particularly proliferous diatom from among algae [Lewin, J., Phycologia, 6, 1–12 (1966), and others], and germanium compounds have been starting to be employed. While germanium proves effective in preventing or inhibiting the growth of certain diatom, it fails to prevent growth of diatom having resistance to toxicity by germanium, green algae, red algae, and others.

There has also been made an attempt to use herbicides as algaecides, but none has proved usable yet for the reason that they are highly toxic to aquatic animals. Diuron is generally used as a herbicide for its inhibitory action on photosynthesis of plants to inhibit the growth of the plants. The minimum inhibitory concentration (MIC) of diuron against growth of microalgae and Cyanophyceae is reportedly from 1.1 to 2.8 µg/ml (1.1–2.8 ppm) [D. M. Paterson et al, Lett. Appl. Microbiol., 7, 87–90 (1988)]. From among various herbicides, Call, D. J. et al [Arch. Environ. Contam. Toxi., 16 (5), 607– 613 (1987)] examined acute toxicity of diuron against fathead minnow, and reported that the amount to kill 50% of the fathead minnow ($LD_{50}$) was 14.2 mg/L (14.2 ppm) at 96 hours and 7.7 mg/L (7.7 ppm) at 192 hours, and that the concentration which did not exert bad influence on juvenile fish and eggs thereof was 33.4 µg/L (0.0334 ppm). This reference has also reported acute toxicity of other known aquatic animals [e.g. $LD_{50}$ (96 hours) of larval striped bass, 0.5 mg/L] and the data therein show rather great diversity concerning sensitivity to diuron among various species of aquatic animals. These prior art references indicate that the MIC of diuron used for algae my display high toxicity depending on the kind and growth stages of aquatic animals, and in view of this, diuron cannot be used for removing and destroying algae disregarding the animals living under water. Accordingly, it has been substantially impossible to use herbicides such as diuron in water for raising aquatic animals for the purpose of inhibiting or preventing emergence and growth of algae without causing any influence on aquatic animals.

Meanwhile, artificial seawater having a composition similar to that of natural seawater has been increasingly used in recent years in place of natural seawater for raising and culturing living organisms in seawater, or studying ecology of them. Even if algae do not exist in artificial seawater at the time of its preparation, algae attached or commensal to the marine animal to be raised in the artificial seawater could grow. The artificial seawater, therefore, cannot always inhibit or prevent emergence of algae.

SUMMARY OF THE INVENTION

Accordingly, the present invention aims at providing a method for inhibiting or preventing emergence and growth of algae. The present invention also aims at providing an antialgal composition capable of inhibiting or preventing emergence and growth of algae.

The present inventors intensively studied and have now found a method capable of resolving the shortcoming seen in the conventional methods for removing and destroying algae, which comprises addition of suitable amounts of a germanium compound and a herbicide to water or applying same to objects to which algae attach, the effect being attributable to the synergistic action of the both components. The present inventors have also found that an antialgal composition containing suitable amounts of a germanium compound and a herbicide, which has been added to water for raising aquatic animals such as artificial seawater is free of the shortcoming observed in the conventional artificial seawater, etc. that they cannot inhibit or prevent emergence and growth of algae. The present invention has been completed based on these findings.

DETAILED DESCRIPTION OF THE INVENTION

That is, the present invention relates to a method for inhibiting or preventing emergence and growth of algae. More particularly, the present invention relates to a method for inhibiting or preventing emergence and growth of algae, which comprises use of a germanium compound and a herbicide.

The present invention also relates to an antialgal composition capable of inhibiting or preventing emergence and growth of algae. More particularly, the present invention also relates to an antialgal composition comprising a germanium compound and a herbicide.

The method and the antialgal composition of the present invention can be used for the inhibition and prevention of emergence and growth of diatom and algae which are capable of photosynthesis. The antialgal composition means a composition capable of inhibition or prevention of emergence and growth of the algae to be mentioned below. The algae are exemplified by green algae (Chlorophyceae) such as Ulva, Chlorella, Scenedesmus, and Spirogyra; Charophyceae such as Chara and Lamprothamniun; Prasinophyceae such as Prasinocladus; Euglenophyceae such as Euglena; Phaeophyceae such as Ectocarpus and Papenfusiella; Chrysophyceae such as Chromulina; Bacillariophyceae such as Arachnoidiscus and Navicula; Xanthophyceae such as Tribonema; Rhaphidophyceae such as Fibrocapsa; red algae (Rhodophyceae) such as Gelidium and Sarcodia; and Cyanophyceae such as Microcystis and Spirulina.

The method of the present invention can be used for both water and objects in or on which algae emerge. In particular, the method is preferably used for water for raising aquatic animals. The water for raising aquatic animals is exemplified by seawater such as natural seawater and artificial seawater, and fresh water such as river water, pond water, lake water, tap water, and rain water. It may comprise water for culturing fish and water for fish for appreciation.

The antialgal composition of the invention can be used not only for water for raising aquatic animals but also fish tank and hull which are subject to emergence and growth of algae. Artificial seawater containing the composition of the present invention is prepared by adding a germanium compound and a herbicide to a salt composition having an element composition similar to that of natural seawater.

The germanium compound to be used in the present invention is preferably a compound easily dissolved in water. Here, the germanium compound is germanium or a compound which is taken in by algae and decomposes into germanium therein. Specifically, it is exemplified by germanium dioxide and germanium chloride. These compounds can be suitably used solely or in combination according to the object of the present invention.

The herbicides to be used in the present invention are advantageously inhibitors of photosynthesis of algae and show low toxicity against aquatic animals. The herbicides are preferably electron transport system inhibitors of photosynthesis, such as 1,10-phenanthroline, diuron [3-(3,4-dichlorophenyl) -1,1-dimethylurea], propanil [N-(3,4-dichlorophenyl)propanamide], (3-chlorophenyl)carbamate, 2 -chloro-4,6-bis(ethylamine)-s-triazine, 2-n-heptyl-4 -hydroxyquinoline N-oxide, piericidine A, salicylaldoxime, hydroxylamine, CCCP, DBTQ, and disalicylidenepropanediamine. Of those, preferred ones are aniline derivatives, and more preferred ones are aniline derivatives having amide bond, with the most preference given to diuron and propanil. These compounds can be suitably used solely or in combination according to the object of the present invention.

The herbicide is used in a proportion of 0.00001–0.2, preferably 0.0001–0.1 by weight based on the germanium compound. Specific amounts are decided according to the object of use.

A germanium compound is added to water for raising aquatic animals at a concentration of 1–100 ppm, preferably 1–10 ppm, and a herbicide is added to water for raising aquatic animals at a concentration of 0.001–0.2 ppm, preferably 0.001–0.1 ppm.

When preparing a composition for artificial seawater, there may be contained, besides germanium compound and herbicide, various salts such as sodium chloride, potassium chloride, sodium bromide, potassium bromide, calcium chloride, magnesium chloride, sodium sulfate, sodium carbonate, and magnesium sulfate [sodium (8–13 g/L), magnesium (0.9–1.6 g/L), calcium (0.3–0.5 g/L), potassium (0.3–0.5 g/L), chlorine (15– 24 g/L), sulfur (0.7–1.2 g/L), bromine (0.04–0.08 g/L), carbon (0.02–0.04 g/L)] instead of main elements of natural seawater, and trace components present in natural seawater such as metal ions (e.g. lithium, stronthium, barium, titanium, molibudene, tungsten, manganese, iron, cobalt, nickel, copper, zinc, alminium) and anions such as ammonium, boron, iodine, and fluorine as inorganic salts. These salts, etc. are preferably comprised in the composition of the invention in a manner such that when dissolved in water, the composition and concentration of each element become as similar as possible to those of natural seawater. It is needless to say that salts, trace components, and/or reagents other than those mentioned above may be contained, or salt concentration may be varied according to the purpose when the water is mainly used for the study of marine animals.

The composition for artificial seawater of the invention may take any form usually employed for a composition for artificial seawater, such as powders, granules, and tablets. The composition may be advantageously prepared by any method used in the fields of pharmaceuticals, agricultural chemicals, and so on. When the composition is dissolved in water to prepare artificial seawater, powders would be the most suitable composition form in view of easy dissolution in water. It may be prepared into granules so as to prevent scattering of fine particles.

The composition for artificial seawater of the present invention is preferably stored in a moisture-proof container, such as a bag made of a moisture-proof synthetic resin such as polyethylene or polypropylene, or that laminated with aluminium. In addition, a metal container may be preferably used upon coating inside with a synthetic resin so as to avoid contamination of trace amounts of metallic impurities.

When the composition of the present invention is coated on a fish net or a hull for inhibiting or preventing emergence and growth of algae, a herbicide is mixed at a ratio of 0.00001– 0.2, preferably 0.0001–0.1 (by weight) relative to a germanium compound. When the composition is used for a fish net, the fish net is preferably immersed in an aqueous solution containing a germanium compound at a concentration of 10–200 ppm and a herbicide at a concentration of 0.01–40 ppm, and when it is used for seacrafts, a germanium compound and a herbicide are preferably added and/or mixed at a concentration of 10–200 ppm and 0.01–40 ppm, respectively, to a paint, etc. and coated on the draft of a ship.

In addition, it may be coated on an ornament such as a stone to be sunk in water in a fish tank to be placed in, for example, aquaria, offices, shops and homes.

The present invention is hereinbelow explained in detail by illustrating experiment examples and examples so as to clarify the effect of the invention. It is to be understood that these examples are for exemplification purpose only, and do not limit the scope of the invention.

EXPERIMENT EXAMPLE

Experiment 1:Effects of germanium dioxide on diatom

Various concentrations of germanium dioxide was added to a medium prepared by adding supplemental nutrition for seawater of Provasoli (ES) to sterile natural seawater [K. Nishizawa, et al ed. Kaiso Kenkyuho, Kyoritsu Shuppan, p. 285 (1979); hereinafter abbreviated as ESM medium]. To the obtained media was added diatom subcultured in a medium for sea diatom prepared by adding silicic acid to TES medium [J. Thycol., 23, 38 (1987, suppl.)], and they were subjected to static culture at 25° C. for 13 days under the irradiation of cool white fluorescent lamp at 6000 luces. The growth of the diatom was visually observed. The results are shown in Table 1.

TABLE 1

| Effects of germanium dioxide on growth of diatom | |
|---|---|
| germanium dioxide (ppm) | growth of diatom[a] |
| 0 | + |
| 50 | − |
| 10 | − |
| 5 | − |
| 2 | − |
| 1 | ± |
| 0.5 | + |
| 0.1 | + |

[a]: growth satisfactory
±: small degree of growth observed
−: no growth observed As a result, diatom showed similar growth in both the medium containing 0.5 ppm or below of germanium dioxide and the medium containing no germanium dioxide. In a medium containing 1 ppm of germanium dioxide, the growth was inhibited, and in a medium containing 2 ppm or more of germanium dioxide, diatom did not grow. To sum, germanium dioxide can inhibit or prevent growth of diatom when it is used alone at a concentration of 1 ppm or more. It was also confirmed that diatom could grow in an ESM medium prepared using natural seawater not sterilized, and germanium dioxide under the same conditions as described above, when the concentration of the germanium dioxide was not more than 100 ppm.

Experiment 2: Effects of diuron and propanil on diatom

Diuron or propanil was added to an ESM medium, and thereto was added a suitable amount of green algae which had been separately cultured in an ESM medium. The medium was subjected to static culture at 25° C. for 13 days under the irradiation of cool white fluorescent lamp at 6000 luces. The growth of the green algae was visually observed. The results are shown in Table 2.

TABLE 2

| Effects of diuron and propanil on growth of green algae | | |
|---|---|---|
| concentration | growth of green algae[a] | |
| (ppm) | diuron | propanil |
| 0 | + | + |
| 20 | − | − |
| 2 | ± | − |
| 0.2 | + | − |
| 0.02 | + | + |
| 0.002 | + | + |

[a]: growth satisfactory
±: small degree of growth observed
−: no growth observed As a result, green algae similarly grew in a medium containing 0.2 ppm or below of diuron or 0.2 ppm or below of propanil, and in a medium without these compounds. In a medium containing 2 ppm of diuron, the growth of green algae was inhibited, and in a medium containing 20 ppm of diuron or 2 ppm or more of propanil, green algae did not emerge. To sum, diuron and propanil can inhibit or prevent emergence of green algae when added alone at a concentration of 2 ppm or more.

Experiment 3: Effects of germanium dioxide and diuron used in conjunction on emergence of algae and on Heavenly damselfish (Pomacentrus Coelestis Jordan et Starks)

To a fish tank (20 L) containing Marine Art® (manufactured by Senju Pharmaceutical Co., Ltd., Japan) having a major element composition similar to that of natural seawater, germanium dioxide (5 ppm) and artificial seawater having various diuron concentrations, 5 Heavenly damselfish and coral powder (2 g) attached by algae were added, and they were raised at 25° C. for 2 months. The algae emerged in the artificial seawater and the state of Heavenly damselfish were observed with time. The results are summarized in Table 3.

TABLE 3

| Effects of germanium dioxide (5 ppm) and diuron used in conjunction on emergence of algae and on Heavenly damselfish | | | |
|---|---|---|---|
| concentration (ppm) | | emergence of algae[a] | |
| germanium dioxide | diuron | 1 month later | 2 month later |
| 0 | 0 | ++ | +++ |
| 5 | 0 | + | ++ |
| 5 | 2 | − | − |
| 5 | 0.2 | − | − |
| 5 | 0.02 | − | − |
| 5 | 0.002 | − | − |
| 5 | 0.001 | − | − |

[a]+++: algae attached to the entire glass surface of tank
++: algae attached to part of the glass surface of tank
+: algae attached to coral powder
−: algae not found As a result, germanium dioxide could not inhibit emergence of algae when it was used alone at a concentration of 5 ppm, at which emergence of diatom could be prevented. On the other hand, when germanium (5 ppm) and diuron were used in conjunction, emergence of algae was inhibited at a diuron concentration of 0.001 ppm or above. Therefrom it follows that emergence of algae could be prevented by the synergistic effect of germanium dioxide and diuron even at a lower concentration, at which the use of either compound alone was unsuccessful in inhibiting or preventing emergence of algae.

As regards Heavenly damselfish, germanium dioxide (5 ppm) alone seems to have had no effect on them. The concomitant use of diuron at a concentration of 0.2 ppm or below did not lead to any effects exerted on them. Based on the above, diuron could be safely used in conjunction with germanium dioxide (5 ppm) at a concentration of from 0.001 ppm to 0.2 ppm.

EXAMPLE 1

An aqueous solution (0.1 ml) of germanium dioxide (0.1 g) and diuron (0.4 g/L) was added to 20 L of tap water containing a dechlorinating agent in a fish tank equipped with an oxygen generator, and 15 goldfish were raised therein for a month at ambient temperature in a room open to the sun. During the raising period, attaching of algae to the glass surface of the tank or emergence of algae in the water in the tank was not observed. None of the goldfish died during the period.

EXAMPLE 2

Composition for use in artificial seawater

Sodium chloride (1000 g), magnesium chloride (500 g), sodium sulfate (180 g), calcium chloride (70 g), potassium chloride (30 g), potassium bromide (4 g), sodium hydrogencarbonate (1 g), sodium thiosulfate (0.1 g), boric acid (5 g), sodium borate (2 g), germanium dioxide (0.25 g), diuron in ethanol (0.5 ml, 1 g/1 L), and 52 mg of a mixture of trace elements [a powder mixture of lithium chloride (10 g), titanium tetrachloride (40 mg), manganese chloride (9 mg), ferric chloride (48 mg), zinc chloride (80 mg), ammonium molybdate (200 mg) and sodium tungstate (21 mg)] were thoroughly mixed. The ethanol was evaporated, and the mixture was placed in a polyethylene bag.

The composition was dissolved in tap water to make the total amount of the artificial seawater 50 L.

EXAMPLE 3

Composition for use in artificial seawater

Sodium chloride (1000 g), magnesium chloride (500 g), sodium sulfate (180 g), calcium chloride (70 g), potassium chloride (30 g), potassium bromide (4 g), sodium hydrogencarbonate (1 g), germanium dioxide (0.5 g), propanil in ethanol (1 ml, 0.1 g/1 L), and 52 mg of a mixture of trace elements [a powder mixture of lithium chloride (10 g), titanium tetrachloride (40 mg), manganese chloride (9 mg), ferric chloride (48 mg), zinc chloride (80 mg), ammonium molybdate (200 mg) and sodium tungstate (21 mg)] were thoroughly mixed. The ethanol was evaporated, and the mixture was placed in a polyethylene bag.

The composition was dissolved in deionized water to make the total amount of the artificial seawater 50 L.

EXAMPLE 4

Five Heavenly damselfish and 2 g of coral powder attached by algae were put in artificial seawater in a 20 L fish tank, which was prepared by using the composition for artificial seawater obtained in Example 2 or Example 3, and they were raised at 25° C. for 2 months. Emergence of algae in the artificial seawater and the state of Heavenly damselfish were monitored with time. No emergence of algae was found in the artificial seawater. Mortality rate of Heavenly damselfish was low, and no onset of diseases was found among them.

The composition for artificial seawater of the present invention, when used in the artificial seawater, showed no toxicity to the marine animal, and prevented emergence and growth of algae.

EXAMPLE 5

Germanium dioxide (5 g) and an ethanol solution (20 ml) of diuron (1 g/L) were added to 100 L of water, and a fish net was immersed in the obtained aqueous solution. After drying, the net was immersed in seawater for 1 month and examined. No algae was found attached to the net.

According to the present invention, emergence and growth of algae which are proliferous in the water for raising aquatic animals can be inhibited or prevented with little influence on aquatic animals, since a herbicide is used at such a low concentration as to cause no toxicity and a germanium compound and a herbicide act synergistically, thus making the method of the present invention safely applicable. In addition, the method is advantageously used by, for example, coating the composition of the present invention on a fish tank in which fish for appreciation is kept, so as to keep good appearance of the tank and to reduce burden of cleaning the tank, and so on, which effect being attributable to the method of the invention which can inhibit and prevent emergence and growth of attached algae.

The composition for artificial seawater of the present invention shows no toxicity to marine animals to be raised in the artificial seawater prepared using the composition of the invention, and can inhibit emergence of algae. Therefore, the composition of the invention can be beneficially used for raising, culture, study, and the like of marine animals.

Moreover, the composition of the present invention which is coated on a fish net, a hull, or the like can result in inhibition and prevention of emergence and growth of algae in the environment where influence on fish, etc. is very little.

What is claimed is:

1. A method for inhibiting or preventing emergence and growth of algae in a fish tank, comprising addition of a germanium compound at a concentration of 1–10 ppm and diuron at a concentration of 0.001–0.2 ppm, said algae being at least one member selected from the group consisting of green algae (Chlorophyceae), Charophyceae, Prasinophyceae, Euglena, Phaeophyceae, Chrysophyceae, Bacillariophyceae, Xanthophyceae, Rhaphidophyceae, red algae (Rhodophyceae) and Cyanophyceae.

2. The method of claim 1, wherein the germanium compound is germanium dioxide.

3. An antialgal composition comprising a germanium compound and diuron wherein the weight ratio of the germanium compound and diuron (germanium compound-:diuron) is 1: 0.00001–0.2 and wherein diuron at a concentration of 0.001–0.2 ppm.

4. The composition according to claim 3, wherein the antialgal composition is artificial seawater.

5. The composition according to claim 3 containing the germanium compound at a concentration of 1–10 ppm and the herbicide at a concentration of 0.001–0.2 ppm.

6. The composition according to claim 3, wherein the germanium compound is germanium dioxide.

7. A method for inhibiting or preventing emergence and growth of algae in a water for raising aquatic animals, comprising addition of a germanium compound at a concentration of 1–10 ppm and diuron at a concentration of 0.001–0.2 ppm of the water, said algae being at least one member selected from the group consisting of green algae (Chlorophyceae), Charophyceae, Prasinophyceae, Euglena, Phaeophyceae, Chrysophyceae, Bacillariophyceae, Xanthophyceae, Rhaphidophyceae , red algae (Rhodophyceae) and Cyanophyceae.

* * * * *